(12) United States Patent
Danilo et al.

(10) Patent No.: US 10,950,222 B2
(45) Date of Patent: Mar. 16, 2021

(54) MULTIMODAL VIDEO SYSTEM FOR GENERATING A PERSONALITY ASSESSMENT OF A USER

(71) Applicant: YOBS TECHNOLOGIES, INC., Los Angeles, CA (US)

(72) Inventors: Raphael Louis Jean Danilo, Los Angeles, CA (US); Prathmesh A. Gat, Pleasanton, CA (US); Aamir K. Goriawala, Atlanta, GA (US)

(73) Assignee: YOBS TECHNOLOGIES, INC., Los Angeles, CA (US)

( * ) Notice: Subject to any disclaimer, the term of this patent is extended or adjusted under 35 U.S.C. 154(b) by 0 days.

(21) Appl. No.: 16/393,628

(22) Filed: Apr. 24, 2019

(65) Prior Publication Data

US 2021/0050000 A1 Feb. 18, 2021

Related U.S. Application Data

(63) Continuation of application No. 16/149,588, filed on Oct. 2, 2018, now abandoned.

(60) Provisional application No. 62/566,738, filed on Oct. 2, 2017, provisional application No. 62/579,757, filed on Oct. 31, 2017.

(51) Int. Cl.
| | |
|---|---|
| *A61B 5/16* | (2006.01) |
| *G10L 15/02* | (2006.01) |
| *G10L 15/06* | (2013.01) |
| *G10L 25/63* | (2013.01) |
| *G06K 9/62* | (2006.01) |

(52) U.S. Cl.
CPC ............ *G10L 15/02* (2013.01); *G10L 15/063* (2013.01); *G10L 25/63* (2013.01); *A61B 5/167* (2013.01); *G06K 9/627* (2013.01)

(58) Field of Classification Search
CPC ............................... A61B 5/167; G06K 9/627
See application file for complete search history.

(56) References Cited

U.S. PATENT DOCUMENTS

| | | | | |
|---|---|---|---|---|
| 6,731,307 | B1 * | 5/2004 | Strubbe | G06N 3/004 704/E17.002 |
| 8,719,006 | B2 * | 5/2014 | Bellegarda | G10L 13/10 704/9 |
| 8,837,687 | B2 * | 9/2014 | Odinak | G10L 15/26 379/88.01 |
| 10,019,653 | B2 * | 7/2018 | Wilf | G06K 9/6256 |
| 10,049,103 | B2 * | 8/2018 | Perez | G10L 25/30 |
| 2002/0045154 | A1 * | 4/2002 | Wood | G09B 23/28 434/350 |
| 2012/0002848 | A1 * | 1/2012 | Hill | A61B 5/167 382/118 |

(Continued)

*Primary Examiner* — Feng-Tzer Tzeng
(74) *Attorney, Agent, or Firm* — Kevin Schraven; Anooj Patel; Hankin Patent Law, APC

(57) ABSTRACT

The present disclosure is directed to a system for generating a personality assessment that uses multimodal behavioral signal processing technology and machine learning prediction technology. This system takes a video as input, processes it through an artificial intelligence software built for extracting hundreds of behavioral features, and consequently generates an accurate and reliable personality assessment with its machine-learning predictive software. The personality assessment is based on the five-factor model (FFM), also known as the big 5 personality traits.

20 Claims, 8 Drawing Sheets

(56) References Cited

U.S. PATENT DOCUMENTS

2014/0337009 A1* 11/2014 Kau ................. G06F 40/253
　　　　　　　　　　　　　　　　　　　　704/9

* cited by examiner

MULTIMODAL VIDEO SYSTEM FOR GENERATING A PERSONALITY ASSESSMENT OF A USER

CROSS REFERENCE PARAGRAPH

This application claims the benefit of U.S. Non-Provisional patent application Ser. No. 16/149,588, filed on Oct. 2, 2018, which claims the benefit of U.S. Provisional Application Nos. 62/566,738, filed Oct. 2, 2017, and 62/579,757, filed on Oct. 31, 2017, the contents of which are incorporated herein by this reference as though set forth in their entirety.

FIELD OF USE

The present disclosure relates generally to systems for automatically generating a personality assessment of a user. More specifically, the present disclosure relates to multi-modal behavioral signal processing technology, which applies various artificial intelligence methods to extract behavioral features, coupled with machine learning prediction models to a video of an individual, and automatically generates an accurate and reliable personality assessment based on scores of the five personality traits found in the five-factor model.

BACKGROUND

Measuring personality traits and developing personality assessments has a long history in psychology, where analysis has been done by asking sets of questions. These question sets have been designed by investigating, among other things, lexical terms that are used in daily communications. Whether consciously or unconsciously, thoughts and behaviors are expressed when communicating with others, either verbally, non-verbally, or using visual expressions. Attempts to develop a knowledge base for personality assessments has led to the field of psychometrics, consisting of the quantitative measurement practices in psychology, behavioral studies, and social sciences. Recently, research in behavioral signal processing (BSP) has focused on automatically measuring personality traits using different behavioral cues that appear in daily communications. BSP is an emerging interdisciplinary research domain that consists of deriving human behavioral informatics from speech, language, video, and audio cues in video.

Currently, those attempting to derive useful and valid behavioral constructs and methodologies have been trained professionals who approach their work in a largely manual, and often time-consuming, method. These attempts result in data and parameters that are difficult to extract, process, and interpret for a single trained professional. This difficulty increases significantly as the quantity of data to analyze increases and/or as the number of individuals whose personality traits are being measured becomes larger. Additionally, issues such as potential biases, lack of expertise, or limited resources can affect trained professionals and result in assessments that are inaccurate and misleading.

Machine learning constitutes the study and computer modeling of learning processes. The advancement of recent technology has allowed for powerful machine-learning prediction models that continue to improve, and learn from, their output, as the data that it obtains and analyzes increases in quantity and quality. While relatively new, many are attempting to apply this technology to solve a host of problems found throughout various fields, such as improving cybersecurity, enhancing recommendation engines, and optimizing self-driving cars.

Thus, what is needed is a new and/or improved system that generates an accurate and time-efficient personality assessment of a person using the research of behavioral signal processing, the data of psychometrics, and the technology of artificial intelligence.

SUMMARY

The following presents a simplified overview of the example embodiments in order to provide a basic understanding of some embodiments of the example embodiments. This overview is not an extensive overview of the example embodiments. It is intended to neither identify key or critical elements of the example embodiments nor delineate the scope of the appended claims. Its sole purpose is to present some concepts of the example embodiments in a simplified form as a prelude to the more detailed description that is presented hereinbelow. It is to be understood that both the following general description and the following detailed description are exemplary and explanatory only and are not restrictive.

In accordance with the embodiments disclosed herein, the present disclosure is directed to a system for generating a personality assessment using behavioral signal processing technology (BSPT); technology that, in broad terms, takes a video as input, processes it through an artificial intelligence software built for extracting hundreds of behavioral features, and consequently generates a personality assessment with its machine-learning predictive software. The personality assessment is based on the five-factor model (FFM), also known as the big 5 personality traits, one of the most widely used measurement models of individual personality in psychometrics and psychology research. The FFM is a dimensional regression model of general personality structure that rates the subject on five dimensions of personality features: openness to experience, conscientiousness, extraversion, agreeableness, and neuroticism. The FFM is multimodal, as those personality features are constructs that exist in the video and may be defined as modals that can be studied and measured individually and collectively. This multimodal design allows for maximized output accuracy of the prediction model by processing, using as input, and optimizing the weight of, all the parameters in the video that may be difficult for the human senses to process.

In a preferred embodiment, BSPT extracts and processes hundreds of behavioral parameters in a video of an individual to make predictions of the personality of the individual. These parameters include, but are not limited to, linguistic features, parts of speech features, word choice, audio features, video features, textual content, visual expressions, and emotion in text.

The use of machine-learning allows the BSPT to learn from the patterns of data previously generated and apply that knowledge to the current input without requiring developers to manually program this knowledge in the BSPT.

In accordance with one embodiment of the present disclosure, there is provided a method for generating a personality assessment for a user from a video input via a computing system. The computing system comprises a processor operable to control the computing system, a data storage operatively coupled to the processor, wherein the data storage is configured to store a plurality of personality data associated with a user, and an input/output device operatively coupled to the processor, wherein the input/output device is configured to receive a plurality of data for transmission to the processor, wherein the input/output device is configured to transmit a plurality of data generated by the processor. The computing system further comprises a feature extraction component operatively coupled to the processor and controlled in part by the processor, wherein the feature extraction component is configured to extract a plurality of feature data from a video of the user, a training component operatively coupled to the processor and controlled in part by the processor, wherein the training component is configured to generate a plurality of trained feature data, and a prediction component operatively coupled to the processor and controlled in part by the processor, wherein the prediction component is configured to generate a personality assessment for the user.

The method comprises receiving, via the input/output device, video input associated with the user and transmitting the video input to the feature extraction component, wherein the video input comprises video data and audio data. The method also comprises generating, via the feature extraction component, a text transcript of at least a portion of the audio data and extracting a plurality of parts of speech (POS) feature data, emotion feature data, and linguistic inquiry word count (LIWC) feature data from the text transcript. The method further comprises extracting, via the feature extraction component, audio feature data from the audio data of the video input and video feature data from the video data of the video input. The input/output device transmits at least a portion of each of the extracted POS feature data, extracted emotion feature data, extracted LIWC feature data, extracted audio feature data, and extracted video feature data to the training component. Each of the POS feature data, emotion feature data, LIWC feature data, audio feature data, and video feature data is subjected to at least one training function by the training component to generate trained feature data therefrom. The input/output device transmits at least a portion of the trained POS feature data, trained emotion feature data, trained LIWC feature data, trained audio feature data, and trained video feature data to the prediction component. At least a portion of the trained POS feature data, trained emotion feature data, trained LIWC feature data, trained audio feature data, and trained video feature data is selectively integrated by the prediction component to generate a personality assessment of the user.

In one embodiment, the method further comprises subjecting each of the extracted POS feature data, emotion feature data, LIWC feature data, audio feature data, and video feature data to a cleaning function by the training component to remove null attribute data therefrom to generate cleaned feature data.

In another embodiment, each of the cleaned POS feature data, emotion feature data, LIWC feature data, audio feature data, and video feature data is subjected to a feature scaling function by the training component to normalize the data to generate scaled feature data therefrom. In one embodiment, each of the cleaned POS feature data, emotion feature data, LIWC feature data, audio feature data, and video feature data is subjected to a z-transformation function by the training component to generate the scaled feature data therefrom. In one other embodiment, each of the cleaned POS feature data, emotion feature data, LIWC feature data, audio feature data, and video feature data is subjected to a range transformation function by the training component to generate the scaled feature data therefrom.

In one embodiment, the method also comprises subjecting each of the scaled POS feature data, emotion feature data, LIWC feature data, audio feature data, and video feature data to a dimension reduction function by the training component to reduce the number of features to be considered to generate reduced feature data therefrom. In a preferred embodiment, each of the scaled POS feature data, emotion feature data, LIWC feature data, audio feature data, and video feature data is subjected to a correlation coefficient function to generate reduced feature data therefrom.

In yet another embodiment, the method comprises subjecting each of the reduced POS feature data, emotion feature data, LIWC feature data, audio feature data, and video feature data to an annotation process by the training component to integrate selected video annotation data therewith to generate annotated feature data therefrom. In a preferred embodiment, the selected video annotation data comprises data associated with at least one personality trait selected from the group consisting of openness to experience, conscientiousness, agreeableness, extraversion, neuroticism, and combinations thereof. In another preferred embodiment, video annotation data associated with each of openness to experience, conscientiousness, agreeableness, extraversion, neuroticism is selectively integrated into each of the reduced POS feature data, emotion feature data, LIWC feature data, audio feature data, and video feature data.

In one embodiment, the trained POS feature data, trained emotion feature data, trained LIWC feature data, trained audio feature data, and trained video feature data are subjected to a classification prediction function by the prediction component to generate the personality assessment of the user. In another embodiment, the trained POS feature data, trained emotion feature data, trained LIWC feature data, trained audio feature data, and trained video feature data are subjected to a regression prediction function by the prediction component to generate the personality assessment of the user.

In one other embodiment, the method comprises storing at least one of extracted feature data associated user, trained feature data associated with the user, the personality assessment of the user, and combinations thereof in the data storage.

In accordance with one embodiment of the present disclosure, there is provided a system for generating a personality assessment for a user from a video input. The system comprises a processor operable to control the computing system, a data storage operatively coupled to the processor, wherein the data storage is configured to store a plurality of personality data associated with a user, and an input/output device operatively coupled to the processor, wherein the input/output device is configured to receive a plurality of data for transmission to the processor, wherein the input/output device is configured to transmit a plurality of data generated by the processor. The system further comprises a feature extraction component operatively coupled to the processor and controlled in part by the processor, wherein the feature extraction component is configured to extract a plurality of feature data from a video of the user, a training component operatively coupled to the processor and controlled in part by the processor, wherein the training component is configured to generate a plurality of trained feature data, and a prediction component operatively coupled to the processor and controlled in part by the processor, wherein the prediction component is configured to generate a personality assessment for the user.

In such embodiment, the input/output device is operable to receive video input associated with the user and transmit the video input to the feature extraction component, wherein the video input comprises video data and audio data, receive a plurality of extracted feature data from the feature extraction component and transmit the plurality of extracted feature data to the training component, and receive a plurality of trained feature data from the training component and transmit the plurality of trained feature data to the prediction component.

The feature extraction component is operable to receive the video input from the input/output device, generate a text transcript of at least a portion of the audio data of the received video input, extract a plurality of parts of speech (POS) feature data, emotion feature data, and linguistic inquiry word count (LIWC) feature data from the text transcript of the audio data, extract audio feature data from the audio data of the video input, and extract video feature data from the video data of the video input.

The training component is operable to receive each of the extracted POS feature data, extracted emotion feature data, extracted LIWC feature data, extracted audio feature data, and extracted video feature data from the input/output device, and subject each of the POS feature data, emotion feature data, LIWC feature data, audio feature data, and video feature data to at least one training function to generate trained feature data therefrom.

The prediction component is operable to receive the trained POS feature data, trained emotion feature data, trained LIWC feature data, trained audio feature data, and trained video feature data from the input/output device, and selectively integrate at least a portion of the trained POS feature data, trained emotion feature data, trained LIWC feature data, trained audio feature data, and trained video feature data to generate a personality assessment of the user.

In one embodiment, each of the extracted POS feature data, emotion feature data, LIWC feature data, audio feature data, and video feature data is subjected to a cleaning function by the training component to remove at least one of null attribute data therefrom to generate cleaned feature data.

In another embodiment, each of the cleaned POS feature data, emotion feature data, LIWC feature data, audio feature data, and video feature data is subjected to a feature scaling function by the training component to normalize the data to generate scaled feature data therefrom.

In one other embodiment, each of the scaled POS feature data, emotion feature data, LIWC feature data, audio feature data, and video feature data is subjected to a dimension reduction function by the training component to reduce the number of features to be considered to generate reduced feature data therefrom.

In one embodiment, each of the reduced POS feature data, emotion feature data, LIWC feature data, audio feature data, and video feature data is subjected to an annotation process by the training component to integrate selected video annotation data therewith to generate annotated feature data therefrom.

In another embodiment, the trained POS feature data, trained emotion feature data, trained LIWC feature data, trained audio feature data, and trained video feature data are subjected to a classification prediction function by the prediction component to generate the personality assessment of the user. In one embodiment, the trained POS feature data, trained emotion feature data, trained LIWC feature data, trained audio feature data, and trained video feature data are subjected to a regression prediction function by the prediction component to generate the personality assessment of the user.

Still other advantages, embodiments, and features of the subject disclosure will become readily apparent to those of ordinary skill in the art from the following description wherein there is shown and described a preferred embodiment of the present disclosure, simply by way of illustration of one of the best modes best suited to carry out the subject disclosure. As it will be realized, the present disclosure is capable of other different embodiments and its several details are capable of modifications in various obvious embodiments all without departing from, or limiting, the scope herein. Accordingly, the drawings and descriptions will be regarded as illustrative in nature and not as restrictive.

BRIEF DESCRIPTION OF THE DRAWINGS

The drawings are of illustrative embodiments. They do not illustrate all embodiments. Other embodiments may be used in addition or instead. Details which may be apparent or unnecessary may be omitted to save space or for more effective illustration. Some embodiments may be practiced with additional components or steps and/or without all of the components or steps which are illustrated. When the same numeral appears in different drawings, it refers to the same or like components or steps.

DETAILED DESCRIPTION OF THE ILLUSTRATIVE EMBODIMENTS

Figure 1:
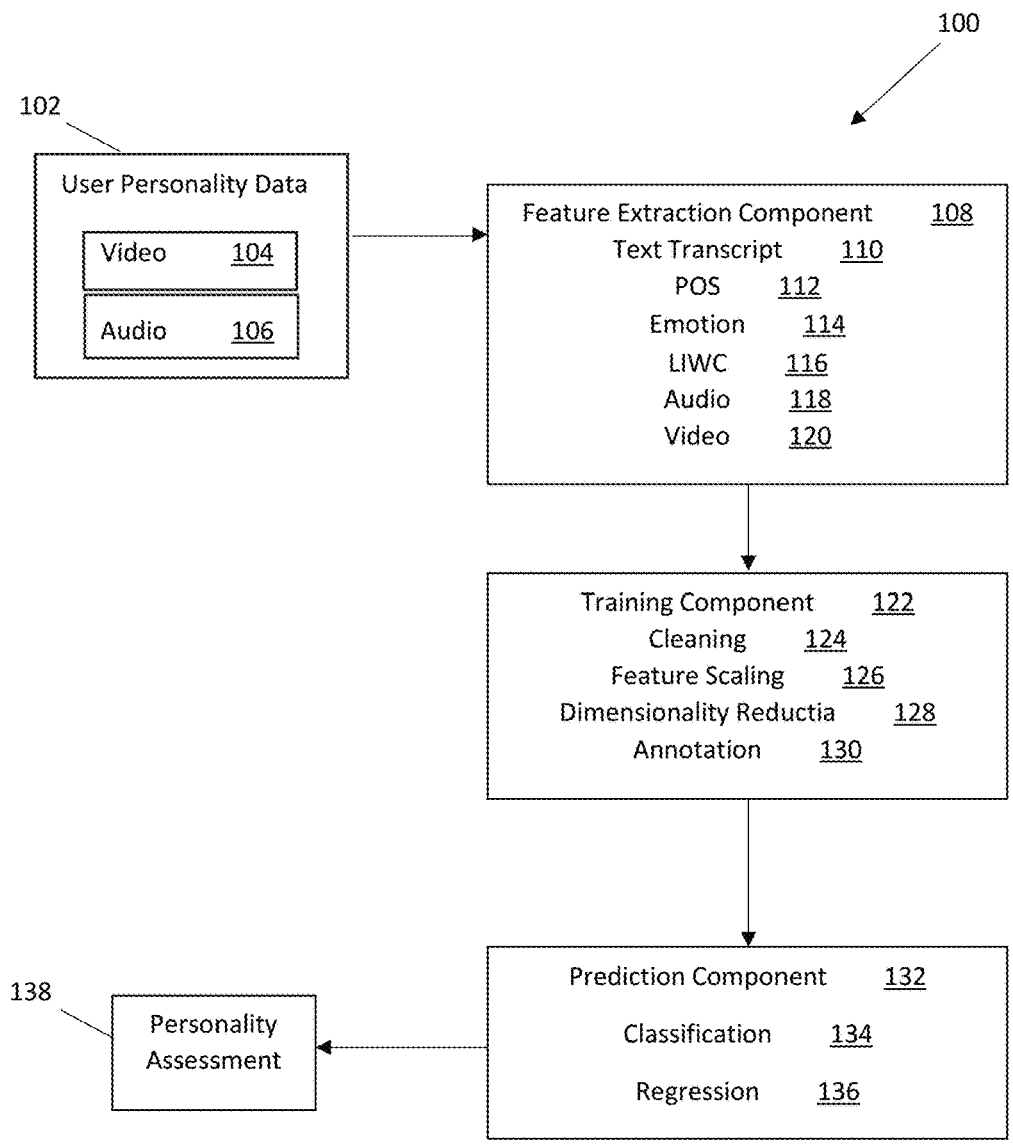
FIG. 1 is an overview of exemplary systems and methods for automatically generating a personality assessment for a user.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that may be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all embodiments of this application including, but not limited to, steps in disclosed methods. Thus, if there are a variety of additional steps that may be performed it is understood that each of these additional steps may be performed with any specific embodiment or combination of embodiments of the disclosed methods.

The present systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware embodiments. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, compact discs, read-only-memory (CD-ROMs), optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, may be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that may direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, may be implemented by special purpose hardware-based computer systems that perform the specified functions or steps, or combinations of special purpose hardware and computer instructions.

In the following description, certain terminology is used to describe certain features of one or more embodiments. For purposes of the specification, unless otherwise specified, the term "substantially" refers to the complete or nearly complete extent or degree of an action, characteristic, property, state, structure, item, or result. For example, in one embodiment, an object that is "substantially" located within a housing would mean that the object is either completely within a housing or nearly completely within a housing. The exact allowable degree of deviation from absolute completeness may in some cases depend on the specific context. However, generally speaking, the nearness of completion will be so as to have the same overall result as if absolute and total completion were obtained. The use of "substantially" is also equally applicable when used in a negative connotation to refer to the complete or near complete lack of an action, characteristic, property, state, structure, item, or result.

As used herein, the terms "approximately" and "about" generally refer to a deviance of within 5% of the indicated number or range of numbers. In one embodiment, the term "approximately" and "about", may refer to a deviance of between 0.001-10% from the indicated number or range of numbers.

Various embodiments are now described with reference to the drawings. In the following description, for purposes of explanation, numerous specific details are set forth in order to provide a thorough understanding of one or more embodiments. It may be evident, however, that the various embodiments may be practiced without these specific details. In other instances, well-known structures and devices are shown in block diagram form to facilitate describing these embodiments.

In accordance with the embodiments disclosed herein, the present disclosure is directed to a system for generating a personality assessment using behavioral signal processing technology (BSPT); technology that, in broad terms, takes a video as input, processes it through an artificial intelligence system configured for extracting hundreds of behavioral features, and consequently generates a personality assessment with its machine-learning predictive software. The personality assessment is based on the five-factor model (FFM), also known as the big 5 personality traits, one of the most widely used measurement models of individual personality in psychometrics and psychology research. The FFM is a dimensional classification model of general personality structure that rates the subject on five dimensions of personality features: openness to experience, conscientiousness, extraversion, agreeableness, and neuroticism. The FFM is multimodal, as those personality features are constructs that exist in the video and may be defined as modals that can be studied and measured individually and collectively. This multimodal design allows for maximized output accuracy of the prediction model by processing, using as input, and optimizing the weight of, all the parameters in the video that may be difficult for the human senses to process.

In a preferred embodiment, BSPT extracts and processes hundreds of behavioral parameters in a video of an individual in order to make predictions of the personality of the individual. These parameters include, but are not limited to, linguistic features, parts of speech features, word choice, audio features, video features, textual content, visual expressions, and emotion in text.

In some embodiments, the present invention provides processes, systems, and method for providing a personality assessment for an individual based on selected personality data received from the individual. FIG. 1 provides an overview 100 of exemplary systems and methods for driving a personality assessment for a user according to the present invention. The process comprises obtaining a plurality of specific personality data associated with the user as shown at 102. In a preferred embodiment, the personality data is obtained from a video of the user answering a number of pre-determined questions. The content of the pre-determined questions may be of any suitable content, wherein the content may be selected by a party requesting the personality assessment, the user undergoing the personality assessment, a third party administering the personality assessment and the like. In a preferred embodiment, the user personality data may include video files 104 and audio files 106, wherein the data stored therein may be used to generate the personality assessment.

In one embodiment, a feature extraction component 108 may extract selected data from the user personality data or video of the user, wherein at least a portion of the extracted data is used in generating the personality assessment. The feature extraction component 108 preferably analyzes the audio files 106 associated with the video and generates a text transcript 110 therefrom. The text transcript 110 may be generated using any suitable speech-to-text application or program. In a preferred embodiment, the feature extraction component 108 analyzes the text transcript 110 to extract Parts of Speech (POS) features data 112, Emotion features data 114, and Linguistic Inquiry Word Count (LIWC) features data 116 therefrom. In one embodiment, the feature extraction component 108 analyzes the audio files 106 to extract Audio features data 118 therefrom. The feature extraction component 108 analyzes the video files 104 to extract Video features data 120 therefrom.

In one embodiment, at least a portion of the POS features data 112, Emotion features data 114, LIWC features data 116, the Audio features data 118, and the Video features data 120 extracted by the feature extraction component 102 are subjected to training by a training component 122 to boost the predictive accuracy of the personality assessment. In a preferred embodiment, each of the five extracted feature datasets are subjected to separate training by the training component 122.

In one embodiment, each extracted feature dataset is subjected to a cleaning process 124 wherein all data points in the feature dataset which have at least one null attribute are removed. In addition, all columns which have the same values through the column are removed. The cleaned dataset is then saved for further processing. For example, the POS features data 112 would be subjected to the cleaning process 124 to generate clean POS features data. The Emotion features data 114, the LIWC features data 116, the Audio features data 118, and the Video features data 120 would each be subjected to a separate cleaning process 124 to generate clean data therefrom.

In another embodiment, each of the cleaned features datasets are subjected to a feature scaling process 126 to appropriately scale the features contained in each dataset. In a preferred embodiment, the cleaned features datasets may be scaled using at least one of a z-transformation scaling function or range transformation scaling function to normalize the data.

In a further embodiment, each of the scaled datasets would be subjected to dimensionality reduction process 128 using a correlation coefficient algorithm to reduce the number of features considered. In the dimensionality reduction process 128, a selected feature is deleted from the dataset if such feature is highly positively or negatively correlated with another feature in order to generate a reduced dimensionality dataset.

In another embodiment, each of the reduced dimensionality datasets is subjected to an annotation process 130, wherein annotated data is integrated into each features dataset. In a preferred embodiment, the annotated data comprises selected data from video annotations associated with the personality traits from the five-factor model (FFM). As an example, video annotations with respect to openness to experience would be integrated into selected trained POS feature data, generating annotated POS feature data directed to openness to experience. As another example, video annotations with respect to conscientiousness would be integrated into selected trained POS data to generate annotated POS feature data directed to conscientiousness. Video annotations associated with extraversion, agreeableness, and neuroticism would also be integrated with selected POS feature data to generate annotated POS feature data directed to each personality trait. Video annotations would also be integrated into each of the trained Emotion feature data, trained LIWC feature data, the trained Audio feature data, and the trained Video feature data to generate annotated feature data directed to each of the five personality traits.

In one embodiment, the annotated feature data for each of the extracted feature datasets is then subjected to a prediction algorithm or prediction component 132 to generate a personality assessment 138 for the user. In a preferred embodiment, at least a portion of the annotated feature data for each of the extracted feature datasets is selectively integrated to generate the personality assessment 138 for the user. In one embodiment, the annotated feature data for each of the extracted feature datasets is subjected to a classification prediction process 134 to generate the personality assessment 138. In another embodiment, the annotated feature data for each of the extracted feature datasets is subjected to a regression prediction process 136 to generate the personality assessment 138.

Figure 2:
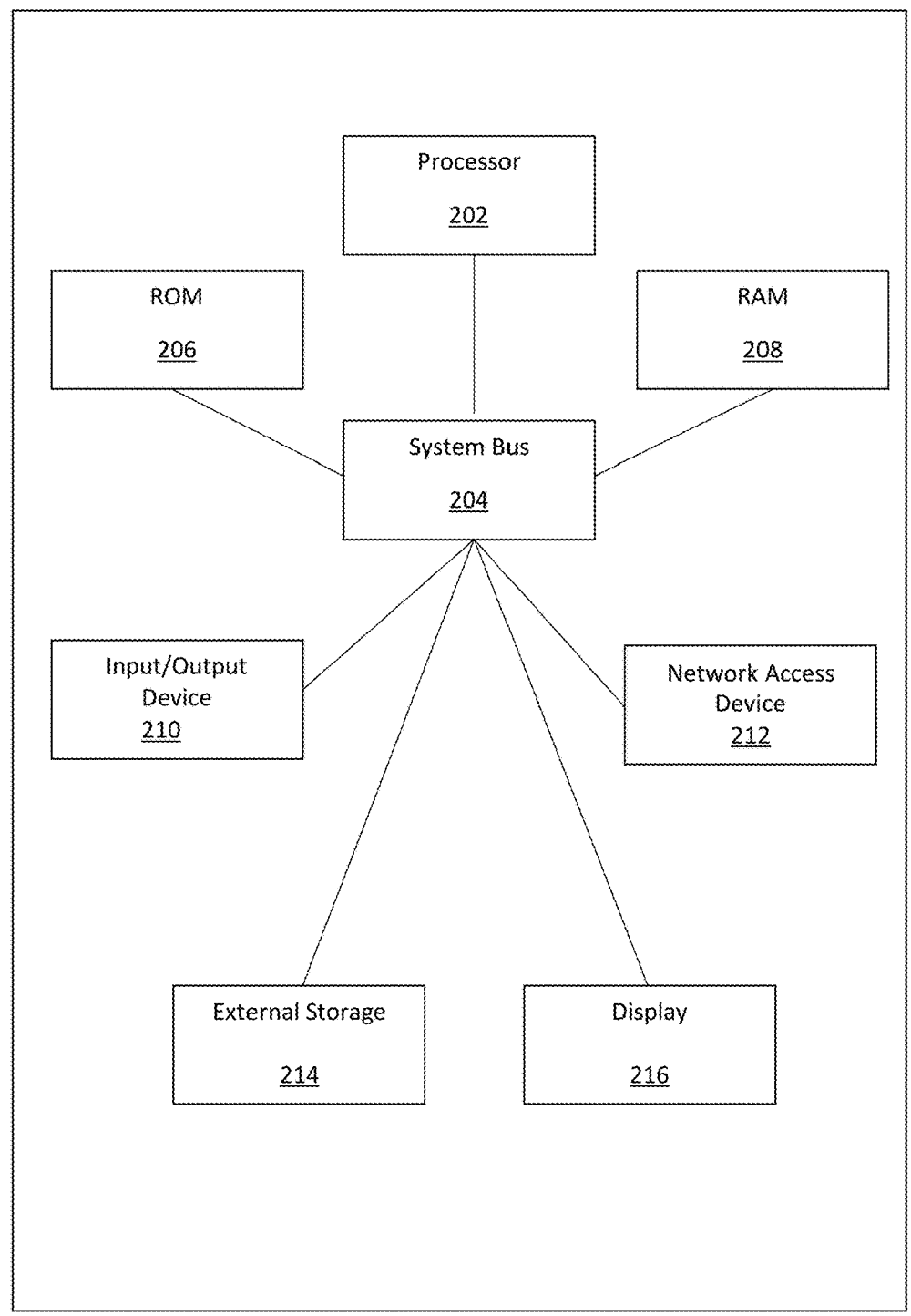
FIG. 2 is a block diagram illustrating an example system environment for automatically generating personality assessments of users.

FIG. 2 is a high-level block diagram illustrating an example system environment for deriving personalized health assessment through integrating genetic information and phenotypic measurements according to the present disclosure. The system 200 is shown as a hardware device, but may be implemented in various forms of hardware, software, firmware, special purpose processors, or a combination thereof. Some embodiments are implemented in software as a program tangibly embodied on a program storage device. By implementing with a system or program, semi-automated or automated workflows are provided to assist a user in generating personalized health assessments.

The system 200 is a computer, personal computer, server, PACs workstation, mobile computing device, imaging system, medical system, network processor, network, or other now know or later developed processing system. The system 200 includes at least one processor 202 operatively coupled to other components via a system bus 204. The processor 202 may be, or may comprise, any suitable microprocessor or microcontroller, for example, a low-power application-specific controller (ASIC) and/or a field programmable gate array (FPGA) designed or programmed specifically for the task of controlling a device as described herein, or a general purpose central processing unit (CPU). In one embodiment, the processor 202 may be implemented on a computer platform, wherein the computer platform includes an operating system and microinstruction code. The various processes, methods, acts, and functions described herein may be either part of the microinstruction code or part of a program (or combination thereof) which is executed via the operating system as discussed below.

The other components include memories (ROM 206 and/or RAM 208), a network access device 212, an external storage 214, an input/output device 210, and a display 216. Furthermore, the system 200 may include different or additional entities.

The input/output device 210, network access device 212, or external storage 214 may operate as an input operable to receive at least a portion of at least one of the genotypic information and the phenotypic measurements. Input may be received from a user or another device and/or output may be provided to a user or another device via the input/output device 210. The input/output device 210 may comprise any combinations of input and/or output devices such as buttons, knobs, keyboards, touchscreens, displays, light-emitting elements, a speaker, and/or the like. In an embodiment, the input/output device 210 may comprise an interface port (not shown) such as a wired interface, for example a serial port, a Universal Serial Bus (USB) port, an Ethernet port, or other suitable wired connection. The input/output device 210 may comprise a wireless interface (not shown), for example a transceiver using any suitable wireless protocol, for example Wi-Fi (IEEE 802.11), Bluetooth®, infrared, or other wireless standard. In an embodiment, the input/output device 210 may comprise a user interface. The user interface may comprise at least one of lighted signal lights, gauges, boxes, forms, check marks, avatars, visual images, graphic designs, lists, active calibrations or calculations, 2D interactive fractal designs, 3D fractal designs, 2D and/or 3D representations, and other interface system functions.

The network access device 212 allows the computing system 200 to be coupled to one or more remote devices (not shown) such as via an access point (not shown) of a wireless network, local area network, or other coupling to a wide area network, such as the Internet. In that regard, the processor 202 may be configured to share data with the one or remote devices via the network access device 212. The shared data may comprise, for example, genetic information, phenotypic information, genetic risk prediction data, and the like. In various exemplary embodiments, the network access device 212 may include any device suitable to transmit information to and from another device, such as a universal asynchronous receiver/transmitter (UART), a parallel digital interface, a software interface or any combination of known or later developed software and hardware. The network access device 212 provides a data interface operable to receive at least a portion of at least one of the genotypic information and the phenotypic measurements.

The processor 202 has any suitable architecture, such as a general processor, central processing unit, digital signal processor, application specific integrated circuit, field programmable gate array, digital circuit, analog circuit, combinations thereof, or any other now known or later developed device for processing data. The processor 202 may be a single device or include multiple devices in a distributed arrangement for parallel and/or serial processing. Likewise, processing strategies may include multiprocessing, multitasking, parallel processing, and the like. A program may be uploaded to, and executed by, the processor 202.

The processor 202 performs the workflows, data manipulation of the genetic information, integration of phenotypic measurements with the genotypic information and/or other processes described herein. The processor 202 operates pursuant to instructions. The genotypic information and the phenotypic measurements may be stored in a computer readable memory, such as the external storage 214, ROM 206, and/or RAM 208. The instructions for implementing the processes, methods and/or techniques discussed herein are provided on computer-readable storage media or memories, such as a cache, buffer, RAM, removable media, hard drive or other suitable data storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Because some of the constituent system components and method acts depicted in the accompanying figures may be implemented in software, the actual connections between the system components (or the process steps) may differ depending upon the manner of programming.

The external storage 214 may be implemented using a database management system (DBMS) managed by the processor 202 and residing on a memory, such as a hard disk, RAM, or removable media. Alternatively, the storage 214 is internal to the processor 202 (e.g. cache). The external storage 214 may be implemented on one or more additional computer systems. For example, the external storage 214 may include a data warehouse system residing on a separate computer system, a PACS system, or any other now known or later developed storage system.

The preferred embodiment of the present disclosure relates to a system for generating a personality assessment of a user. The system may include obtaining and storing a video from a URL provided by a user, the video consisting of the user answering pre-determined questions. The system may also include storing the video as an mp4 video file, obtaining and storing a way audio file from the mp4 video file, obtaining and storing a text transcript from the way audio file, obtaining and storing one or more parts of speech features from the text transcript, obtaining and storing one or more emotional content from the text transcript, obtaining and storing one or more linguistic inquiry word count from the text transcript, and obtaining and storing one or more audio features from the way audio file.

Augmenting the Performance of Personality Assessment Prediction

The following examples are provided in order to demonstrate and further illustrate certain preferred embodiments and aspects of the present disclosure and are not to be construed as limiting the scope thereof.

In one embodiment, the feature extraction component 108 may implement a feature extraction (FE) process to extract various features from a video of the user. These features are in turn used by various machine-learning models to predict personality using the five-factor model (FFM). In a preferred embodiment, the FE process consists of eight steps. In the first step, the video is downloaded from a URL or other network resource, which is sent as a parameter to the FE process. The downloaded video is stored in a Resources/Videos folder as an MP4 video file. If the video cannot be downloaded, then the FE process is terminated.

The second step consists of the Video FE job initiation. This step uploads the video to Affectiva using an API call to Affectiva. Once the video is uploaded, Affectiva initiates a Video feature extraction job and returns the job index URL as part of the API response. Once the API call is completed, a Job Log is created in affectivaJobLog Collection, along with relevant information like videoId, Affectiva index URL, and Job Status (working). If the Affectiva Job Log is not created, the FE process is terminated.

In the third step, the audio extraction is performed. This is done by the Way audio file being obtained from the downloaded MP4 video file. The audio file is then saved in a Resources/AudioFiles folder. If the audio file cannot be obtained, then the FE process is terminated.

The fourth step consists of the text transcript extraction. In this step, the transcript is obtained from the Way audio file obtained in step two. In order to obtain the transcript, IBM Speech-to-Text API is used. The audio file in Way format is sent to IBM Speech-to-Text API, and it returns the text transcript. If the transcript cannot be obtained, the FE process is terminated.

The fifth step requires the extraction of Parts of Speech (POS) from the transcript obtained in step 3. POS features include pronoun fraction in transcript, verb fraction in transcript, adjective fraction in transcript, past tense fraction in transcript, present tense fraction in transcript, future tense fraction in transcript, adverb fraction in transcript, and noun fraction in transcript. In order to obtain these features, the Natural Language Toolkit library is used; wherein each word in the transcript is given a POS Tag and then a fraction of each POS feature type is calculated. The POS features obtained are stored in a posFeatures collection. If the POS features are not obtained, then the FE process is terminated.

In step six, the emotional content from the text transcript obtained in step three is captured. WordNet database is used for tagging emotions per word in transcript. Following are the emotion types that are used for tagging words in the transcript: anger, disgust, fear, joy, sadness, surprise, anticipation, and neutral. After tagging emotion for each word, the fraction of each emotion in transcript is calculated. This calculation allows for the following features to be stored in a emotionFeatures database: natural sentiment score, compound sentiment score, joy fraction, fear fraction, sadness fraction, surprise fraction, disgust fraction, anger fraction, positive sentiment score, neutral fraction, negative sentiment score, and anticipation fraction. Sentiment scores are obtained using a VADER Sentiment Analysis. If the emotion features are not obtained, then the FE process is terminated.

Step seven consists of obtaining Linguistic Inquiry Word Count (LIWC) features from an LIWC application programming interface (API). This is accomplished by passing as parameter the transcript obtained in step three through the LWIC API to obtain the following LIWC features: "imaginative": 23.344295441878188; "netspeak_focus": 32.011481204553185; "persuasive": 53.50984719172264; "liberal": 43.18869757951088; "self_assured": 66.53239035659955; "body_focus": 97.87017241131832; "trusting": 12.191096145948583; "organized": 57.852103915343044; "type_a": 81.07806808513168; "clout": 45.710506; "family_oriented": 35.010860183509486; "disciplined": 53.37820079348934; "neuroticism": 85.97507368175538; "cooperative": 19.575619471151967; "social_skills": 16.916332347151116; "openness": 26.966434607045482; "cold": 90.98913537707332; "adjustment": 48.64461674964664; "aggressive": 84.41332785915486; "depression": 24.92664032316692; "food_focus": 36.90316610452883; "generous": 16.823669912510404; "sexual_focus": 38.59850307933812; "power_driven": 61.170149628143506; "work_oriented": 42.390487026454956; "friend focus": 30.301344646823317; "religion_oriented": 35.14827527205458; "analytic": 60.06186; "extraversion": 25.725560524852852; "agreeableness": 8.976123697709676; "happiness": 8.293723957395967; "ambitious": 58.29648364289841; "emotionalTone": 7.2753305; "artistic": 46.86243064676693; "independent": 95.7858428481148; "melancholy": 65.82995524190224; workhorse": 77.24983481027392; "reward_bias": 50.533564393939386; "energetic": 26.233131469488175; "self conscious": 94.16967127262231; "assertive": 46.788767832215264; "insecure": 83.39315330797311; "leisure_oriented": 35.10828580132849; "videoId": "26"; "impulsive": 29.977501024674787; "emotionally aware": 80.25538848218783; "intellectual": 38.425856389422904; "conscientiousness": 64.76570050263072; "active": 44.81730488218997; "thinking style": 67.02432134406013; "dutiful": 39.39430775354387; "genuine": 12.081778760610584; authentic": 98.8293; adventurous": 32.89546820092367; "sociable": 31.861241662422078; "cheerful": 30.686186452485572; "cautious": 86.37735102282764; "empathetic": 20.32090905924756; "humble": 53.86688288843811; "friendly": 26.854333394682662; "anxious": 69.31100460676258; "money_oriented": 40.10074153450545; "stressed": 80.9355990948734; and "health_oriented": 44.50970381245589. These features are stored in a liwcFeatures Collection folder. If the LIWC features are not obtained, then the FE process is terminated.

Finally, in step eight, the Audio features are obtained from the Way audio file obtained in step two. Audio features include zero crossing rate, energy, entropy of energy, spectral centroid, spectral spread, spectral entropy, spectral flux, spectral rolloff, Mel-frequency cepstral coefficients, chroma vector, chroma deviation, delta energy, total speech time, and average speech window time. The following libraries are used to extract these features: pyAudioAnalysis, pySoundFile, and vad-python. If the Audio features are not obtained, then the FE process is terminated.

Natural Language Toolkit is a leading platform for building Python programs to work with human language data. It provides easy-to-use interfaces to over 50 corpora and lexical resources such as WordNet, along with a suite of text processing libraries for classification, tokenization, stemming, tagging, parsing, semantic reasoning, and wrappers for industrial-strength natural language processing libraries.

VADER (Valence Aware Dictionary and Sentiment Reasoner) Sentiment Analysis is a fully open-sourced lexicon and rule-based sentiment analysis tool that is specifically attuned to sentiments expressed in social media.

An Application Programming Interface (API) is a set of subroutine definitions, protocols, and tools for building application software. In broad terms, it allows two software programs to communicate with each other.

Affectiva is an emotion measurement technology company that grew out of MIT's Media Lab, which has developed a way for computers to recognize human emotions based on facial cues or physiological responses.

The prediction of personality traits requires the use of Multimodal information, such as visual, audio, POS, LIWC, and emotion. In order to use this information, five separate datasets of video are required, one for each information type. Initially, this information is obtained from the FE process and is stored in the database. However, in order to apply machine-learning algorithms, these datasets need to be pre-processed using the training component 122 to create a Training Dataset.

The training component 122 consists of data cleaning and the pre-processing pipeline, which takes Feature Dataset as input (audio, video, LIWC, emotion, and POS) and provides a final Training Dataset for each model. The training process for a single dataset is comprised of five steps. In the first step an entire Feature dataset is obtained from an associated database. Step two consists of cleaning the dataset. This cleaning process 124 removes all data points from the Feature dataset obtained in the previous step that have at least one null attribute. This process also removes columns that have the same values through the column. The cleaned dataset is saves as Features-cleaned.csv. Step three includes the feature scaling process 126, which supports two types of feature scaling: Z Transformation and Range Transformation. Depending upon the Flag, the appropriate feature scaling algorithm is applied to the dataset in order to obtain the final, feature-scaled dataset. Step four includes the dimensionality reduction process 128. In this step the dimensionality of the dataset obtained in step three is reduced by using a correlation coefficient algorithm. Using this algorithm, a feature is deleted if it is highly positively/negatively correlated with some other feature in order to obtain a final reduced dataset. Step five comprises the annotation process 130, wherein annotated data is selectively integrated with the dataset obtained from step four on VideoId to obtain the final Training Dataset. The annotated data consists of calculated FFM scores from video annotations using Ten-Item Personality Measure technology, a brief, academically validated measure of the Big 5 personality dimensions.

The prediction component 132 then selectively integrates at least a portion of the annotated feature data for each of the extracted feature datasets to generate the personality assessment 138 for the user. In one embodiment, the annotated feature data for each of the extracted feature datasets is subjected to a classification prediction process 134 to generate the personality assessment 138. In another embodiment, the annotated feature data for each of the extracted feature datasets is subjected to a regression prediction process 136 to generate the personality assessment 138.

The Classification prediction process 134 is responsible for prediction of the Big-5 personality traits for a given candidate. The output of this route is a Big 5 personality classification value, each value being either 0 or 1. The process works as follows: the route takes candidateId and clientId as input, validates it, and multimodalCalculation method of the global MultimodalClassification object created at the application start is invoked, by passing videoId. A MultimodalCalculation method from the object created in step four is invoked, which performs the following actions: Obtains Lock,Set videoId to passed videoId parameter, loading features from the video (emotion, video, audio, POS, LIWC), obtaining Big 5 classification prediction values for each of the feature types, calculating final Big 5 personality traits by taking polling of each of the features, and returning a final Big 5 personality json. This json is returned to the API caller, along with candidateId and clientId.

The Regression prediction process 136 takes candidateId and clientId as input, validates both, and invoke multimodalCalculation method of MultimodalRegression object created at the application start, by passing videoId. A Multimodal Calculation method from the objects is invoked, which performs the following actions: Obtains Lock,Set videoId to passed videoId parameter, loading features from the video (emotion, video, audio, POS, LIWC), obtaining Big 5 classification prediction values for each of the feature types, calculating final Big 5 personality traits by taking polling of each of the features, and returning a final Big 5 personality json. This j son is returned to the API caller, along with candidateId and clientId.

The use of a machine-learning approach allows the BSPT to learn from the patterns of data previously generated and apply that knowledge to the current input.

In one embodiment, the system for generating a personality assessment may use BSPT to take audio as input, process it through its machine-learning software, and generate a personality assessment.

Figure 3:
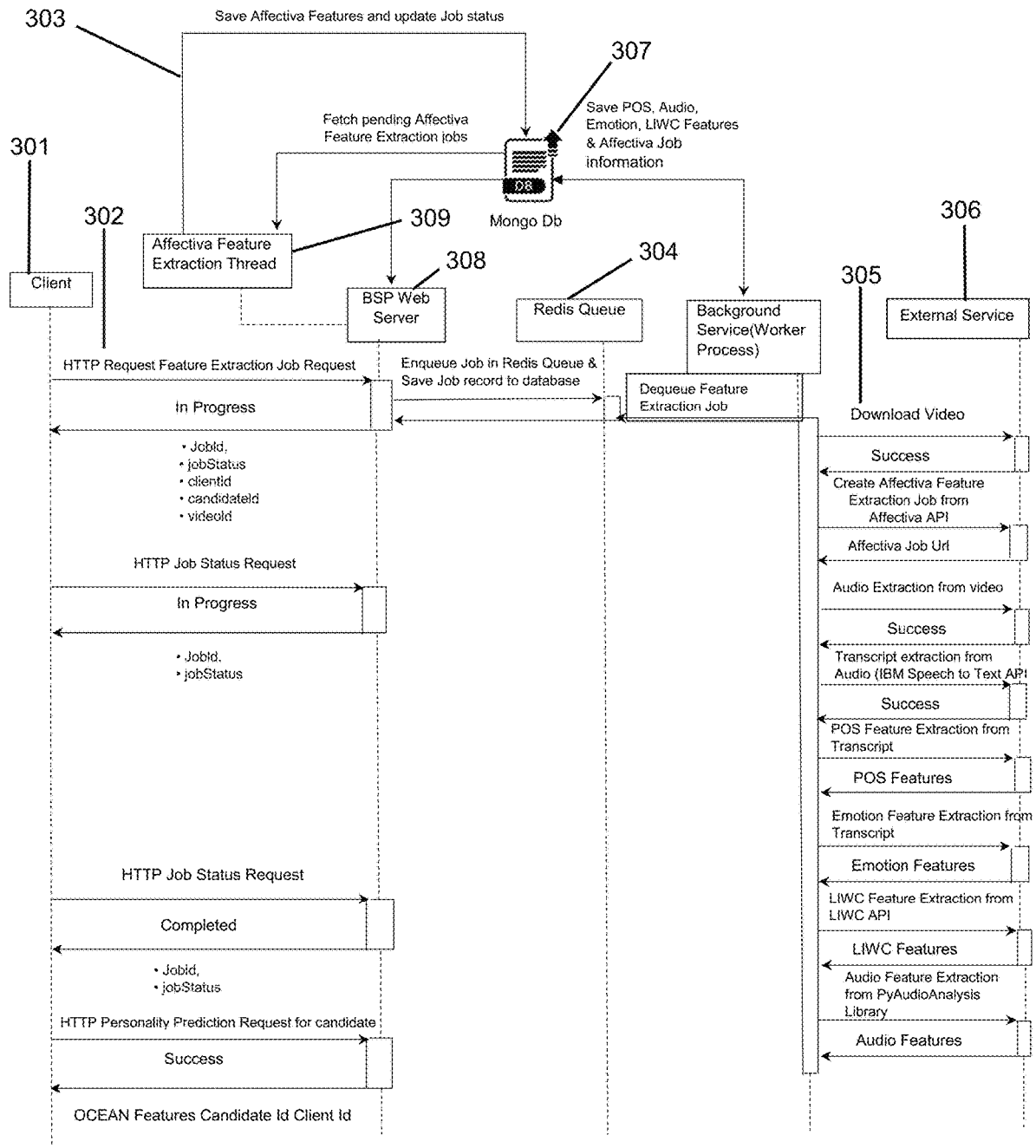
FIG. 3 is a block diagram of one embodiment of a system for generating a personality assessment of a user.

FIG. 3 is a schematic diagram of one embodiment of a system for generating a personality assessment 138 of a user as described herein. A Client 301 provides a video to the Video Storage 701, with the video consisting of the Client 301 answering pre-determined questions. The HTTP application 302 accepts the video, and initiates a Feature Extraction Job Request, a Job Status Request, and a Personality Prediction Request. The HTTP application 302 is in communication with the BSP Web Server 308 and the Redis Queue 304 to confirm that the Feature Extraction Request, the Job Status Request, and the Personality Prediction Request are all completed. The BSP Web Server 308 is in communication with the Mongo Database 307, which is a document database used for querying and indexing. The Mongo Database 107 allows for the fetching and saving of Feature Extraction information 303, including inputting and receiving output from the Affectiva Feature Extraction Thread 309. The Mongo Database 307 provides the update of the Feature Extraction and Job Status Requests, receiving input from the Feature Extraction Process 305. The Feature Extraction Process 305 requires the use of External Services 306. The External Services 306 take the various feature extractions and provide separate datasets for each step. The External Services 306 may comprise IBM Speech-to-Text 401 and LIWC API 402. However, the Feature Extraction Process 305 may use Internal Services in place of External Services 306.

Figure 4:
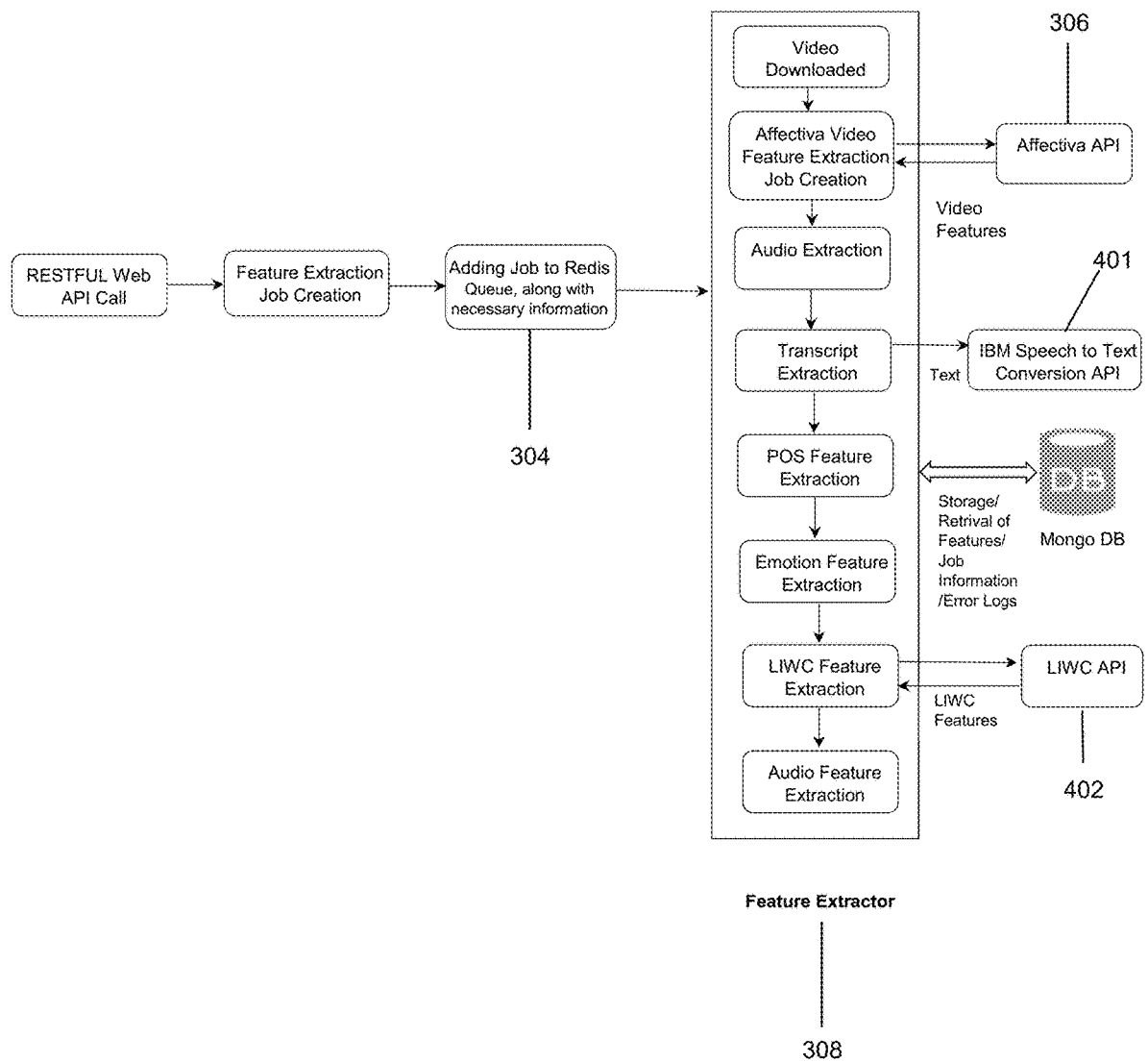
FIG. 4 is a block diagram of one embodiment of the system for generating a personality assessment of a user.

FIG. 4 is a block diagram of one embodiment of a system for generating a personality assessment of a user as described herein. The Redis Queue 304 is also responsible for providing input to the Feature Extraction Process 305. The Feature Extraction Process 305 requires the use of External Services 306, which take the various feature extractions and provide separate datasets for each step. The External Services 306 may comprise IBM Speech-to-Text 401 and LIWC API 402. The Feature Extraction Process 305 may provide individual datasets, such as the video download, the audio extraction, transcript extraction, POS features extraction, Emotion Feature Extraction, LIWC feature extraction, audio feature extraction, and the Affectiva video feature extraction.

Figure 5:
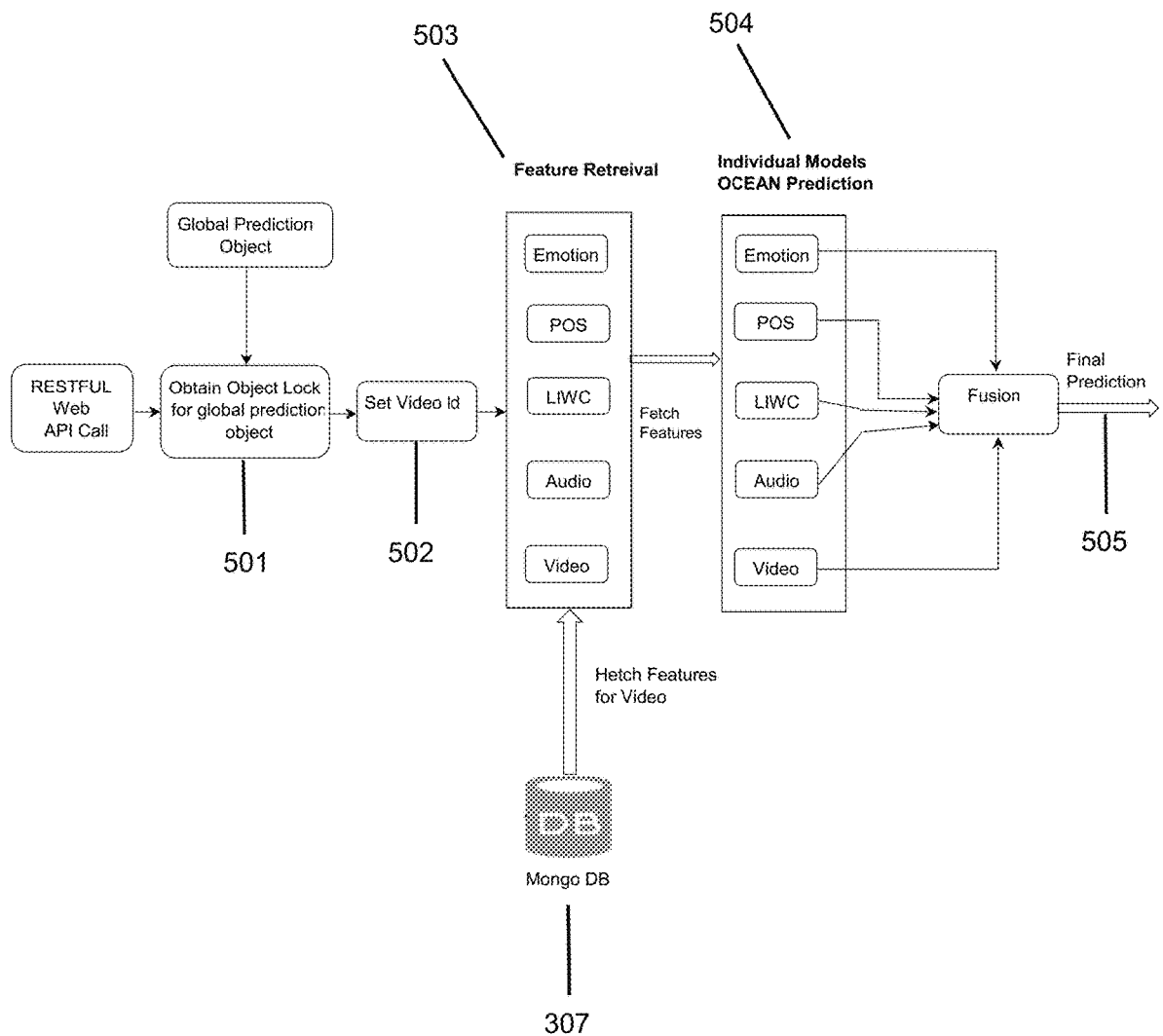
FIG. 5 is a block diagram of one embodiment of a Prediction Route of the system for generating a personality assessment of a user.

FIG. 5 is a block diagram of one embodiment of a Prediction Route of the system for generating a personality assessment of a user. The Prediction Route may be comprised of the Model Loading, obtaining Lock, setting videoId 502, the Feature Retrieval Process 503, the Individual Prediction 504, and the Final Prediction 505. The Prediction Route requires the use of Models, stored in the cache 501, for each of the separate datasets. The Prediction Route applies each of these Models to their respective individual Feature Extraction datasets, retrieved from the Mongo database 307. The Models provide prediction for their respective datasets to provide the overall Individual Prediction 504, comprised of five datasets, Video, LIWC, POS, and Emotion, Audio datasets. Each of these datasets are then inputted into the Final Prediction 505, which outputs the Personality Predictor for the Client 301.

Figure 6:
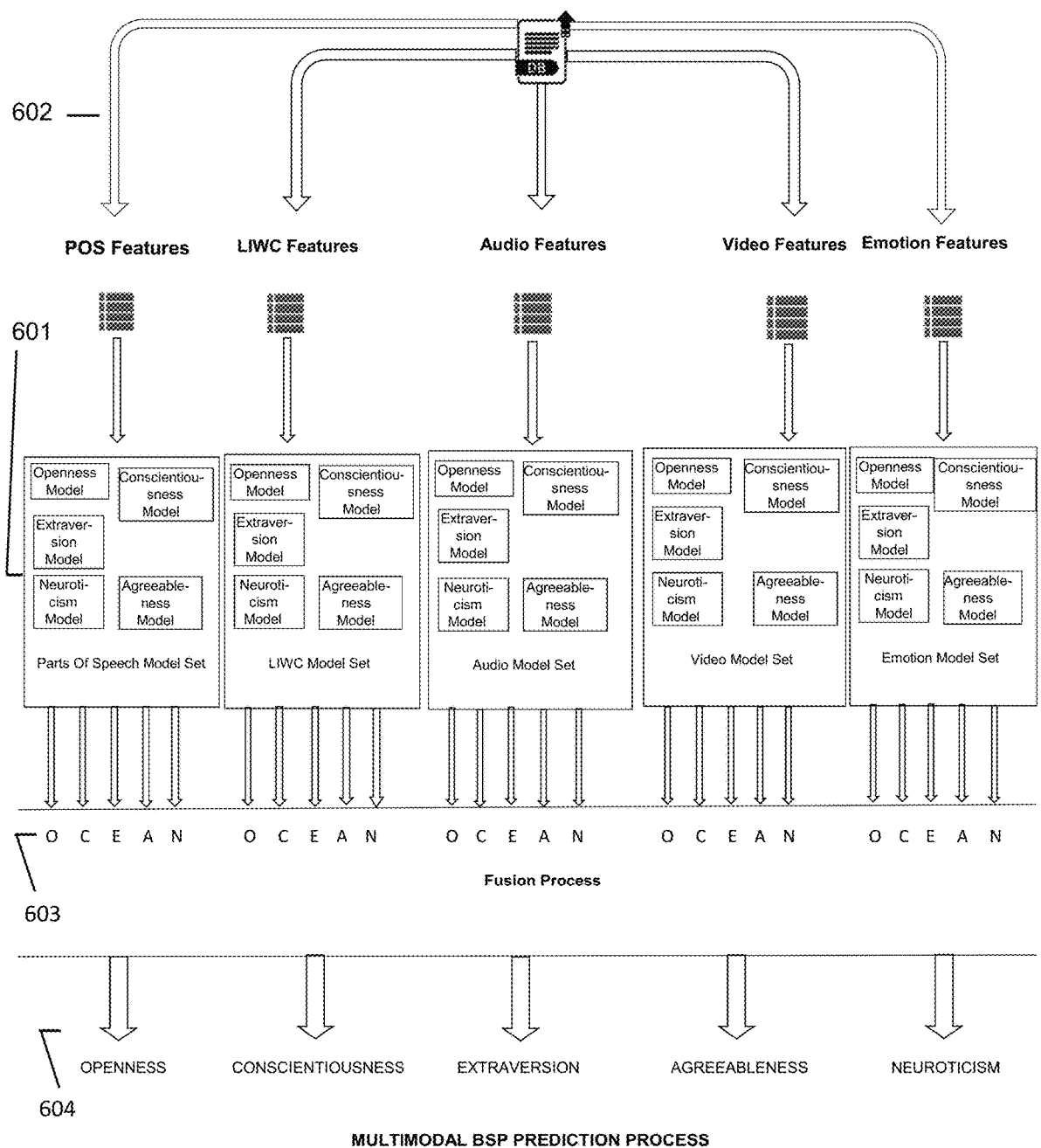
FIG. 6 is a block diagram of one embodiment of a Multimodal BSP Prediction Process of the system for generating a personality assessment of a user.

FIG. 6 is a block diagram of one embodiment of a Multimodal BSP Prediction Process of the system for generating a personality assessment of a user. The Multimodal BSP Prediction Process applies the individual model sets 601 retrieved from the Model Loading 502 and applies them to their respective individual Feature Extraction datasets 602 obtained from the Feature Retrieval 503. The output of the application of the models to the individual datasets goes through a Fusion Process 603, which results in the calculation for each of the big 5 Personality Traits Classifications 604.

Figure 7:
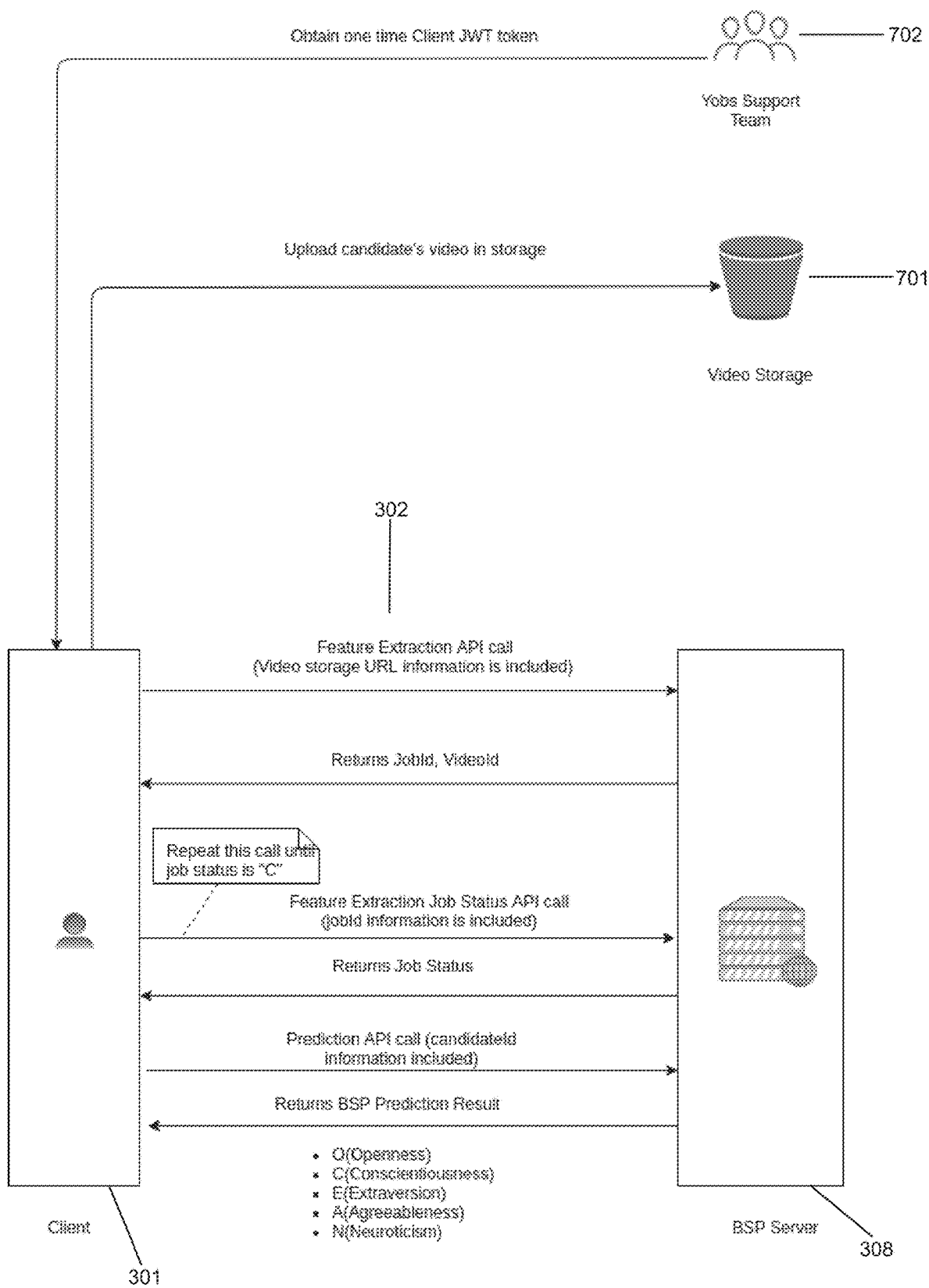
FIG. 7 is a block diagram of one embodiment of a Client BSP API Process of the system for generating a personality assessment of a user.

FIG. 7 is a block diagram of one embodiment of a Client BSP API Process of the system for generating a personality assessment of a user. The Client 301 provides a video to the Video Storage 701, with the video consisting of the Client 701 answering pre-determined questions. The HTTP application 302 accepts the video and initiates a Feature Extraction Job Request, a Job Status Request, and a Personality Prediction Request. The HTTP application 302 is in communication with the BSP Web Server 308 to confirm that the Feature Extraction Request, the Job Status Request, and the Personality Prediction Request are all completed. The Client 301 may also be in communication with the Support Team 702 to, among other things, obtain a one-time client JWT token.

Figure 8:
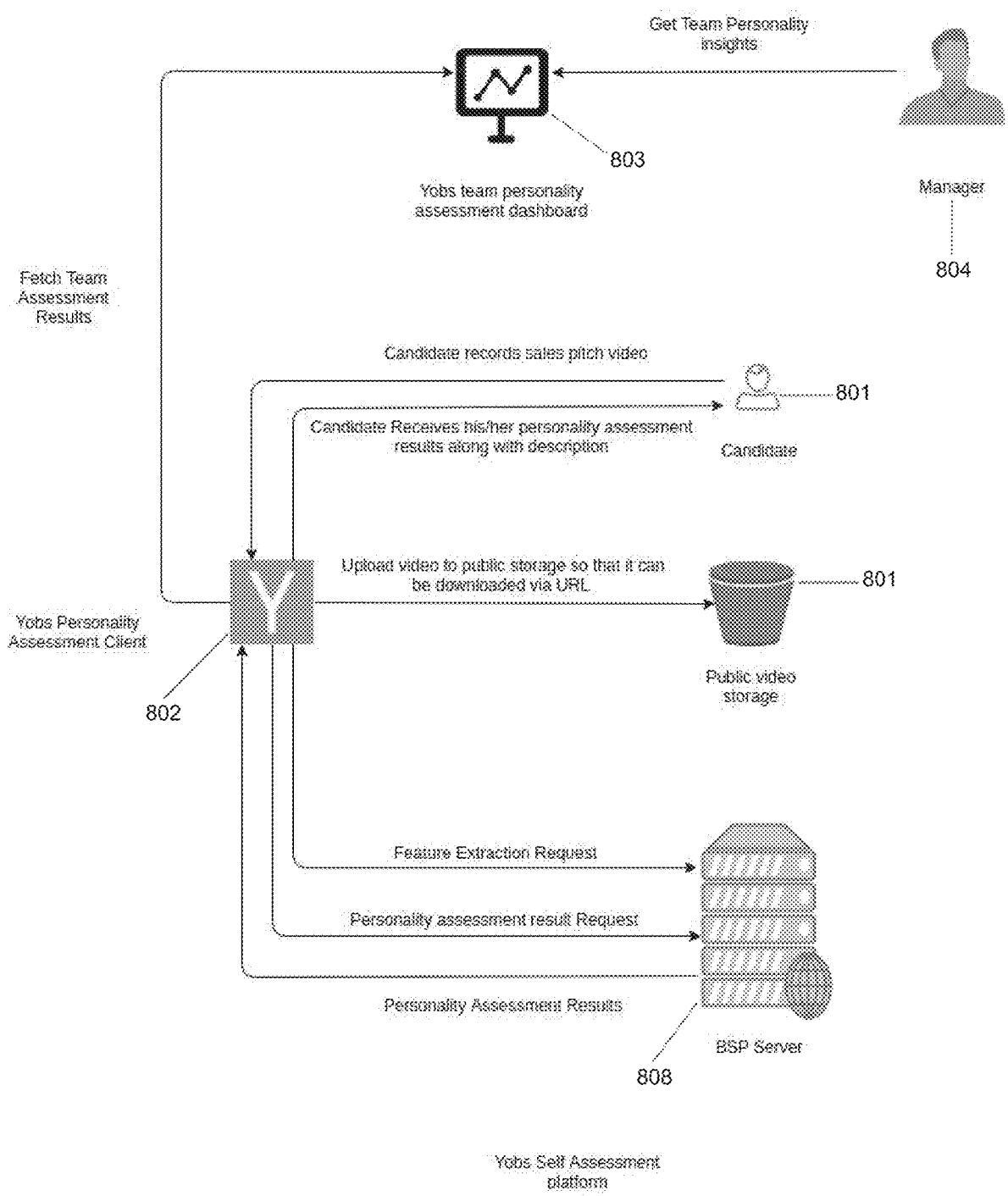
FIG. 8 is a schematic diagram of one embodiment of a Self-Assessment Platform of the system for generating a personality assessment of a user.

FIG. 8 is a schematic diagram of one embodiment of a Self-Assessment Platform of the system for generating a personality assessment of a user. A Candidate 801, inputs a video to a Personality Assessment Client 802, which then saves the video to a Video Storage 701. The Personality Assessment Client 802 sends a Feature Extraction Request and a Personality Assessment Result Request to a BSP Server 308, which then returns a Personality Assessment Result to the Personality Assessment Client 802. The Personality Assessment Client 802 can also be in communication with a Team Personality Assessment Dashboard 803. A Manager 804 can be in direct control of the Team Personality Assessment Dashboard 803, such that the Team Personality Assessment Dashboard 803 takes as input information from the Personality Assessment Client 802 and provides output to the Personality Assessment Client 802.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure. As used in the specification and in the claims, the singular form of "a", "an", and "the" include plural referents unless the context clearly dictates otherwise.

Unless otherwise stated, all measurements, values, ratings, positions, magnitudes, sizes, locations, and other specifications that are set forth in this specification, including in the claims that follow, are approximate, not exact. They are intended to have a reasonable range that is consistent with the functions to which they relate and with what is customary in the art to which they pertain.

In addition, the various illustrative logical blocks, modules, and circuits described in connection with certain embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, system-on-a-chip, or state machine. A processor may also be implemented as a combination of computing devices, e.g., a combination of a DSP and a microprocessor, a plurality of microprocessors, one or more microprocessors in conjunction with a DSP core, or any other such configuration.

Operational embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, a DVD disk, or any other form of storage medium known in the art. An exemplary storage medium is coupled to the processor such the processor may read information from, and write information to, the storage medium. In the alternative, the storage medium may be integral to the processor. The processor and the storage medium may reside in an ASIC or may reside as discrete components in another device.

Furthermore, the one or more versions may be implemented as a method, apparatus, or article of manufacture using standard programming and/or engineering techniques to produce software, firmware, hardware, or any combination thereof to control a computer to implement the disclosed embodiments. Non-transitory computer readable media may include but are not limited to magnetic storage devices (e.g., hard disk, floppy disk, magnetic strips), optical disks (e.g., compact disk (CD), digital versatile disk (DVD)), smart cards, and flash memory devices (e.g., card, stick). Those skilled in the art will recognize many modifications may be made to this configuration without departing from the scope of the disclosed embodiments.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those of ordinary skill in the art that various modifications and variations may be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method for generating a personality assessment for a user from video input thereof, via a computing system, wherein the computing system comprises:
    (a) a processor operable to control the computing system,
    (b) a data storage operatively coupled to the processor, wherein the data storage is configured to store a plurality of personality data associated with a user,
    (c) an input/output device operatively coupled to the processor, wherein the input/output device is configured to receive a plurality of data for transmission to the processor, wherein the input/output device is configured to transmit a plurality of data generated by the processor,
    (d) a feature extraction component operatively coupled to the processor and controlled in part by the processor, wherein the feature extraction component is configured to extract a plurality of feature data from a video of the user,
    (e) a training component operatively coupled to the processor and controlled in part by the processor, wherein the training component is configured to generate a plurality of trained feature data, and
    (f) a prediction component operatively coupled to the processor and controlled in part by the processor, wherein the prediction component is configured to generate a personality assessment for the user, the method comprising:
    receiving, via the input/output device, video input associated with the user and transmitting the video input to the feature extraction component, wherein the video input comprises video data and audio data;
    generating, via the feature extraction component, a text transcript of at least a portion of the audio data of the received video input;
    extracting, via the feature extraction component, a plurality of parts of speech (POS) feature data, emotion feature data, and linguistic inquiry word count (LIWC) feature data from the text transcript of the audio data;
    extracting, via the feature extraction component, audio feature data from the audio data of the video input;
    extracting, via the feature extraction component, video feature data from the video data of the video input;
    transmitting, via the input/output device, at least a portion of each of the extracted POS feature data, extracted emotion feature data, extracted LIWC feature data, extracted audio feature data, and extracted video feature data to the training component;
    subjecting each of the POS feature data, emotion feature data, LIWC feature data, audio feature data, and video feature data to at least one training function by the training component to generate trained feature data therefrom;
    transmitting, via the input/output device, at least a portion of the trained POS feature data, trained emotion feature data, trained LIWC feature data, trained audio feature data, and trained video feature data to the prediction component; and
    selectively integrating at least a portion of the trained POS feature data, trained emotion feature data, trained LIWC feature data, trained audio feature data, and trained video feature data by the prediction component to generate a personality assessment of the user.

2. The method of claim 1, further comprising subjecting each of the extracted POS feature data, emotion feature data, LIWC feature data, audio feature data, and video feature data to a cleaning function by the training component to remove at least one of null attribute data therefrom to generate cleaned feature data.

3. The method of claim 2, further comprising subjecting each of the cleaned POS feature data, emotion feature data, LIWC feature data, audio feature data, and video feature data to a feature scaling function by the training component to normalize the data to generate scaled feature data therefrom.

4. The method of claim 3, wherein each of the cleaned POS feature data, emotion feature data, LIWC feature data, audio feature data, and video feature data is subjected to a z-transformation function by the training component to generate the scaled feature data therefrom.

5. The method of claim 3, wherein each of the cleaned POS feature data, emotion feature data, LIWC feature data, audio feature data, and video feature data is subjected to a range transformation function by the training component to generate the scaled feature data therefrom.

6. The method of claim 3, further comprising subjecting each of the scaled POS feature data, emotion feature data, LIWC feature data, audio feature data, and video feature data to a dimension reduction function by the training component to reduce the number of features to be considered to generate reduced feature data therefrom.

7. The method of claim 6, wherein each of the scaled POS feature data, emotion feature data, LIWC feature data, audio feature data, and video feature data is subjected to a correlation coefficient function to generate reduced feature data therefrom.

8. The method of claim 6, further comprising subjecting each of the reduced POS feature data, emotion feature data, LIWC feature data, audio feature data, and video feature data to an annotation process by the training component to integrate selected video annotation data therewith to generate annotated feature data therefrom.

9. The method of claim 8, wherein the selected video annotation data comprises data associated with at least one personality trait selected from the group consisting of openness to experience, conscientiousness, agreeableness, extraversion, neuroticism, and combinations thereof.

10. The method of claim 9, wherein video annotation data associated with each of openness to experience, conscientiousness, agreeableness, extraversion, neuroticism is selectively integrated into each of the reduced POS feature data, emotion feature data, LIWC feature data, audio feature data, and video feature data.

11. The method of claim 1, wherein the trained POS feature data, trained emotion feature data, trained LIWC feature data, trained audio feature data, and trained video feature data are subjected to a classification prediction function by the prediction component to generate the personality assessment of the user.

12. The method of claim 1, wherein the trained POS feature data, trained emotion feature data, trained LIWC feature data, trained audio feature data, and trained video feature data are subjected to a regression prediction function by the prediction component to generate the personality assessment of the user.

13. The method of claim 1, further comprising storing at least one of extracted feature data associated user, trained feature data associated with the user, the personality assessment of the user, and combinations thereof in the data storage.

14. A system for generating a personality assessment for a user from video input thereof, the system comprising
a processor operable to control the computing system;
a data storage operatively coupled to the processor, wherein the data storage is configured to store a plurality of personality data associated with a user;
an input/output device operatively coupled to the processor, wherein the input/output device is configured to receive a plurality of data for transmission to the processor, wherein the input/output device is configured to transmit a plurality of data generated by the processor;
a feature extraction component operatively coupled to the processor and controlled in part by the processor, wherein the feature extraction component is configured to extract a plurality of feature data from a video of the user;
a training component operatively coupled to the processor and controlled in part by the processor, wherein the training component is configured to generate a plurality of trained feature data; and
a prediction component operatively coupled to the processor and controlled in part by the processor, wherein the prediction component is configured to generate a personality assessment for the user;
wherein the input/output device is operable to:
receive video input associated with the user and transmit the video input to the feature extraction component, wherein the video input comprises video data and audio data,
receive a plurality of extracted feature data from the feature extraction component and transmit the plurality of extracted feature data to the training component,
receive a plurality of trained feature data from the training component and transmit the plurality of trained feature data to the prediction component;
wherein the feature extraction component is operable to:
receive the video input from the input/output device,
generate a text transcript of at least a portion of the audio data of the received video input,
extract a plurality of parts of speech (POS) feature data, emotion feature data, and linguistic inquiry word count (LIWC) feature data from the text transcript of the audio data,
extract audio feature data from the audio data of the video input, and
extract video feature data from the video data of the video input;
wherein the training component is operable to:
receive each of the extracted POS feature data, extracted emotion feature data, extracted LIWC feature data, extracted audio feature data, and extracted video feature data from the input/output device, and
subject each of the POS feature data, emotion feature data, LIWC feature data, audio feature data, and video feature data to at least one training function to generate trained feature data therefrom;
wherein the prediction component is operable to:
receive the trained POS feature data, trained emotion feature data, trained LIWC feature data, trained audio feature data, and trained video feature data from the input/output device, and
selectively integrate at least a portion of the trained POS feature data, trained emotion feature data, trained LIWC feature data, trained audio feature data, and trained video feature data to generate a personality assessment of the user.

15. The system of claim 14, wherein each of the extracted POS feature data, emotion feature data, LIWC feature data, audio feature data, and video feature data is subjected to a cleaning function by the training component to remove at least one of null attribute data therefrom to generate cleaned feature data.

16. The system of claim 15, wherein each of the cleaned POS feature data, emotion feature data, LIWC feature data, audio feature data, and video feature data is subjected to a feature scaling function by the training component to normalize the data to generate scaled feature data therefrom.

17. The system of claim 16, wherein each of the scaled POS feature data, emotion feature data, LIWC feature data, audio feature data, and video feature data is subjected to a dimension reduction function by the training component to reduce the number of features to be considered to generate reduced feature data therefrom.

18. The system of claim 17, wherein each of the reduced POS feature data, emotion feature data, LIWC feature data, audio feature data, and video feature data is subjected to an annotation process by the training component to integrate selected video annotation data therewith to generate annotated feature data therefrom.

19. The system of 14, wherein the trained POS feature data, trained emotion feature data, trained LIWC feature data, trained audio feature data, and trained video feature data are subjected to a classification prediction function by the prediction component to generate the personality assessment of the user.

20. The system of claim 14, wherein the trained POS feature data, trained emotion feature data, trained LIWC feature data, trained audio feature data, and trained video feature data are subjected to a regression prediction function by the prediction component to generate the personality assessment of the user.

* * * * *